United States Patent
Enoki et al.

(10) Patent No.: US 11,850,000 B2
(45) Date of Patent: Dec. 26, 2023

(54) OPHTHALMIC SURGERY MICROSCOPE SYSTEM, CONTROL DEVICE, AND CONTROL METHOD

(71) Applicant: SONY CORPORATION, Tokyo (JP)

(72) Inventors: Junichiro Enoki, Tokyo (JP); Yoshio Soma, Tokyo (JP); Tomoyuki Ootsuki, Tokyo (JP)

(73) Assignee: SONY CORPORATION, Tokyo (JP)

( * ) Notice: Subject to any disclaimer, the term of this patent is extended or adjusted under 35 U.S.C. 154(b) by 562 days.

(21) Appl. No.: 17/049,458

(22) PCT Filed: Mar. 27, 2019

(86) PCT No.: PCT/JP2019/013313
§ 371 (c)(1),
(2) Date: Oct. 21, 2020

(87) PCT Pub. No.: WO2019/216049
PCT Pub. Date: Nov. 14, 2019

(65) Prior Publication Data
US 2021/0251483 A1    Aug. 19, 2021

(30) Foreign Application Priority Data
May 7, 2018    (JP) .................................. 2018-089088

(51) Int. Cl.
*A61B 3/13*    (2006.01)
*A61B 3/103*    (2006.01)
*A61B 3/14*    (2006.01)

(52) U.S. Cl.
CPC ................ *A61B 3/13* (2013.01); *A61B 3/103* (2013.01); *A61B 3/14* (2013.01)

(58) Field of Classification Search
CPC ......... A61F 9/007; G02B 21/22; G02B 21/36; A61B 3/13; A61B 3/103; A61B 3/14; A61B 3/12
(Continued)

(56) References Cited

U.S. PATENT DOCUMENTS

| 7,423,807 B2 * | 9/2008 | Sander ...................... A61B 3/13 351/216 |
| 2007/0299429 A1 * | 12/2007 | Amano .............. G02B 27/0093 606/4 |

(Continued)

FOREIGN PATENT DOCUMENTS

| JP | 08-194189 A | 7/1996 |
| JP | 2003-322803 A | 11/2003 |
| JP | 2018-051210 A | 4/2018 |

OTHER PUBLICATIONS

International Search Report and Written Opinion of PCT Application No. PCT/JP2019/013313, dated Jun. 25, 2019, 07 pages of ISRWO.

*Primary Examiner* — William R Alexander
(74) *Attorney, Agent, or Firm* — CHIP LAW GROUP

(57) ABSTRACT

The stereoscopic effect of an image presented in accordance with an additional optical system is compensated for. There is provided an ophthalmic surgery microscope system including: a surgical microscope that observes an inside of an eye from a pupil, and magnifies and presents a real image; an additional optical system selectively arranged between the surgical microscope and the pupil; an imaging unit that acquires the real image presented by the surgical microscope as an image; a presentation unit that stereoscopically presents the image; and a control unit that changes a vertical magnification control value for adjusting a vertical magni- (Continued)

fication of the real image in accordance with a detection result of the additional optical system.

11 Claims, 12 Drawing Sheets

(58) Field of Classification Search
USPC .......................................................... 351/206
See application file for complete search history.

(56) References Cited

U.S. PATENT DOCUMENTS

| | | | | |
|---|---|---|---|---|
| 2010/0152847 | A1* | 6/2010 | Padrick | A61B 3/13 623/6.11 |
| 2012/0197102 | A1* | 8/2012 | Hanebuchi | A61B 3/13 600/398 |
| 2014/0132922 | A1* | 5/2014 | Padrick | A61B 3/152 351/208 |
| 2018/0055356 | A1* | 3/2018 | Shibata | G02B 21/368 |
| 2018/0168447 | A1* | 6/2018 | Ishinabe | A61B 3/102 |
| 2018/0289254 | A1* | 10/2018 | Matsunobu | A61B 3/0075 |
| 2019/0282091 | A1* | 9/2019 | Matsunobu | A61B 3/13 |
| 2019/0313902 | A1* | 10/2019 | Charles | A61B 3/0025 |

\* cited by examiner (CONCAVE LENS IS USED)    (CONVEX LENS IS USED)

OPHTHALMIC SURGERY MICROSCOPE SYSTEM, CONTROL DEVICE, AND CONTROL METHOD

CROSS REFERENCE TO RELATED APPLICATIONS

This application is a U.S. National Phase of International Patent Application No. PCT/JP2019/013313 filed on Mar. 27, 2019, which claims priority benefit of Japanese Patent Application No. JP 2018-089088 filed in the Japan Patent Office on May 7, 2018. Each of the above-referenced applications is hereby incorporated herein by reference in its entirety.

TECHNICAL FIELD

The present disclosure relates to an ophthalmic surgery microscope system, a control device, and a control method.

BACKGROUND ART

In retina and vitreous surgery, in order to obtain a wide operative field image of fundus, an additional optical system (so-called wide-view lens) is provided in a surgical microscope, and a wide-angle observation system for observing a real image created by the additional optical system is used. For example, in a case where a wide-view lens of 120D is used, it is said that a lateral magnification (magnification in a plane vertical to an optical axis) becomes ½ times of that in a case where the additional optical system is not provided in consideration of the refractive index of a crystalline lens or cornea, and a four times wider operative field can be obtained. A vertical magnification (magnification in the optical-axis direction), which influences the unevenness level of an image, is expressed by the square of the lateral magnification, and becomes ¼ times of that in a case where the additional optical system is not provided.

As described above, in a case where an additional optical system is provided in a wide-angle observation system, a wide operative field image of fundus can be obtained while stereoscopic effects are lost. For this reason, in a case where an elaborate operation such as a treatment of removing macular pucker of a macula part and inner limiting membrane (ILM) peeling is performed, the wide-angle observation system is sometimes not used, or lenses of different magnifications are sometimes used at present.

For example, Patent Document 1 discloses a surgical microscope that calculates the virtual image position of a display image in a stereoscopic image display apparatus and controls the virtual image position of the stereoscopic image display apparatus on the basis of the imaging state of a stereoscopic image capturing apparatus or a detection result and operation amount of an operation of changing a display state.

CITATION LIST

Patent Document

Patent Document 1: Japanese Patent Application Laid-Open No. 2003-322803

SUMMARY OF THE INVENTION

Problems to be Solved by the Invention

Unfortunately, although stereoscopic effects of a stereoscopic image can be adjusted by the technique described in Patent Document 1, providing an additional optical system in a surgical microscope is not considered, and change in the stereoscopic effects depending on the presence or absence of an additional optical system is not compensated for.

Consequently, the disclosure proposes a new and improved ophthalmic surgery microscope system, control device, and control method capable of compensating for the stereoscopic effects of an image presented in accordance with an additional optical system.

Solutions to Problems

According to the disclosure, there is provided an ophthalmic surgery microscope system including: a surgical microscope that observes an inside of an eye from a pupil, and magnifies and presents a real image; an additional optical system selectively arranged between the surgical microscope and the pupil; an imaging unit that acquires the real image presented by the surgical microscope as an image; a presentation unit that stereoscopically presents the image; and a control unit that changes a vertical magnification control value for adjusting a vertical magnification of the real image in accordance with a detection result of the additional optical system.

Furthermore, according to the disclosure, there is provided a control device including a control unit that: detects an additional optical system selectively arranged between a surgical microscope and a pupil, the surgical microscope observing an inside of an eye from the pupil, and magnifying and presenting a real image; changes a vertical magnification control value for adjusting a vertical magnification of the real image in accordance with a detection result of the additional optical system; and adjusts a vertical magnification of an image of the real image acquired by the imaging unit on the basis of the vertical magnification control value.

Moreover, according to the disclosure, there is provided a control method including: detecting an additional optical system selectively arranged between a surgical microscope and a pupil, the surgical microscope observing an inside of an eye from the pupil, and magnifying and presenting a real image; changing a vertical magnification control value for adjusting a vertical magnification of the real image in accordance with a detection result of the additional optical system; and adjusting a vertical magnification of an image of the real image acquired by the imaging unit on the basis of the vertical magnification control value.

Effects of the Invention

As described above, according to the disclosure, the stereoscopic effects of an image presented in accordance with an additional optical system can be compensated for. Note that the above-described effect is not necessarily limitative, and, along with or in place of the above-described effect, any of the effects illustrated in the present specification, or other effects that can be grasped from the specification may be exhibited.

MODE FOR CARRYING OUT THE INVENTION

Preferred embodiments of the disclosure will be described in detail below with reference to the accompanying drawings. Note that, in the specification and the drawings, components having substantially the same functional configuration will be assigned the same signs, and redundant description will be omitted.

Note that the description will be given in the following order.
1. First Embodiment (Presentation Side Adjustment)
1.1. Outline of Ophthalmic Surgery Microscope System
1.2. Functional Configuration
1.3. Control Method
2. Second Embodiment (Imaging Side Adjustment)
2.1. Functional Configuration
2.2. Control Method
3. Conclusion
4. Hardware Configuration

1. FIRST EMBODIMENT

[1.1. Outline of Ophthalmic Surgery Microscope System]

Figure 1:
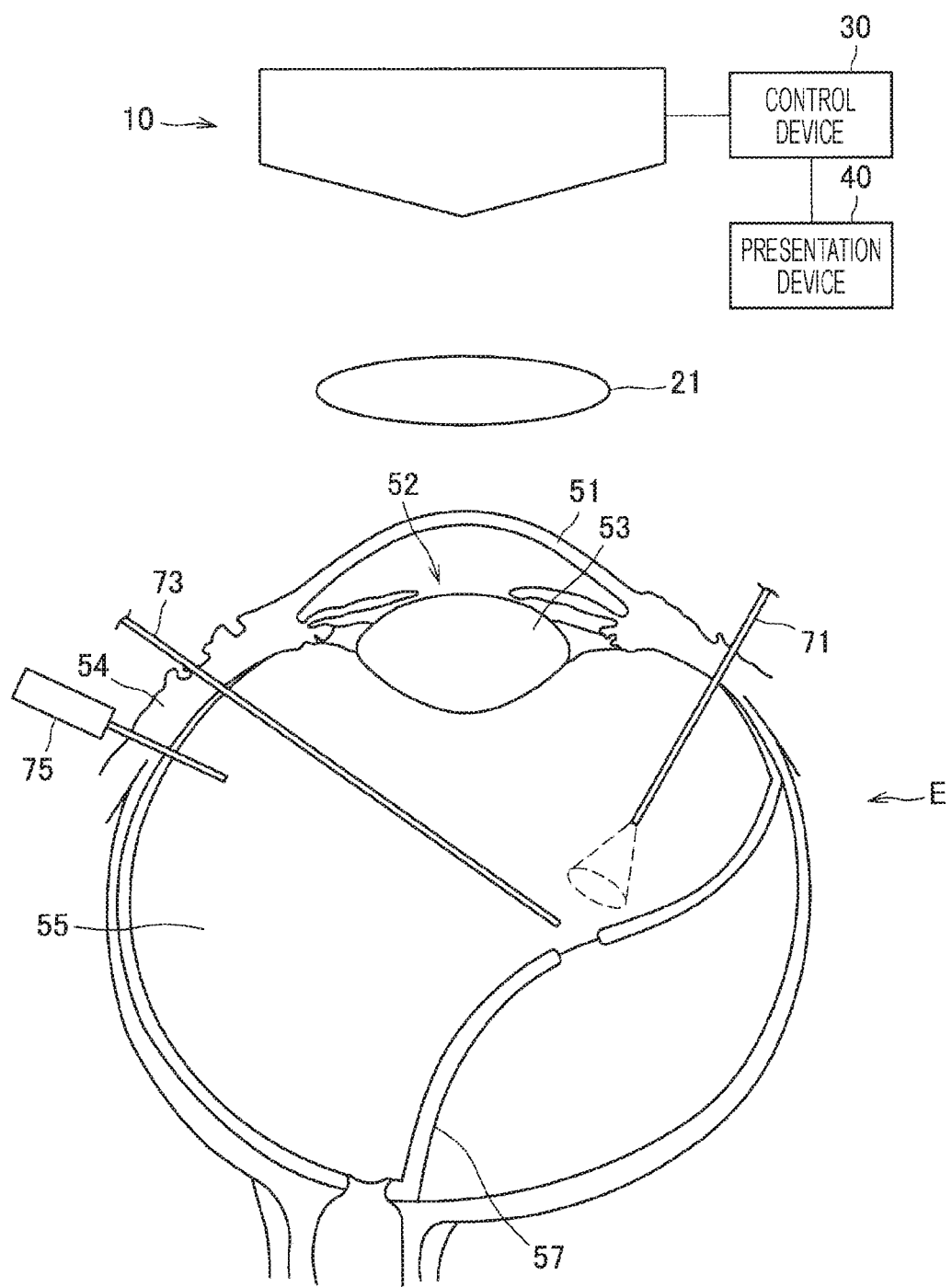
FIG. 1 is an explanatory view illustrating a situation of ophthalmic surgery performed with an eye of a subject being observed through a surgical microscope by using an additional optical system in an ophthalmic surgery microscope system according to the first embodiment of the disclosure.
Figure 2:
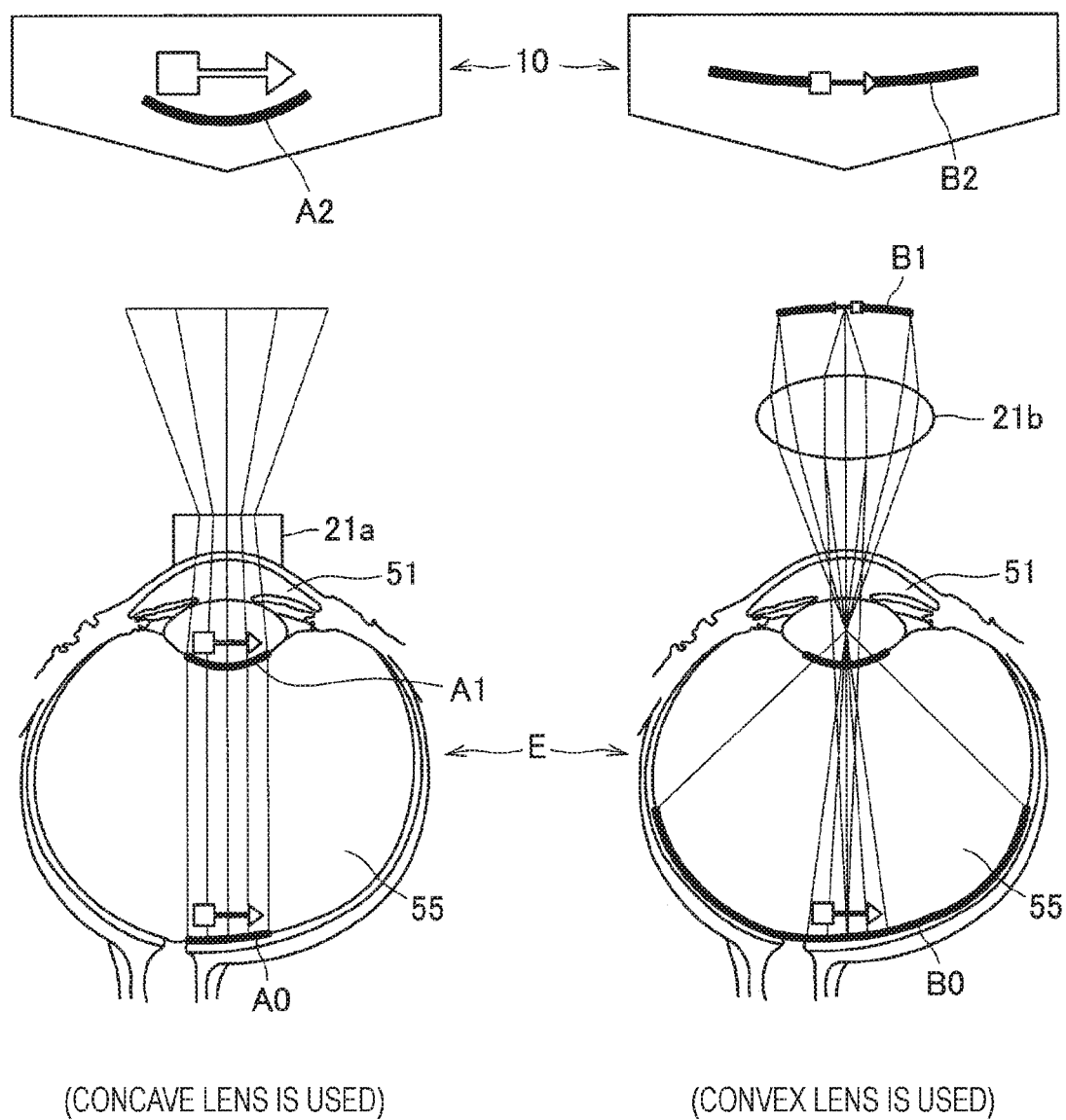
FIG. 2 is an explanatory view illustrating changes in lateral magnification and vertical magnification of a real image caused by the additional optical system.
Figure 3:
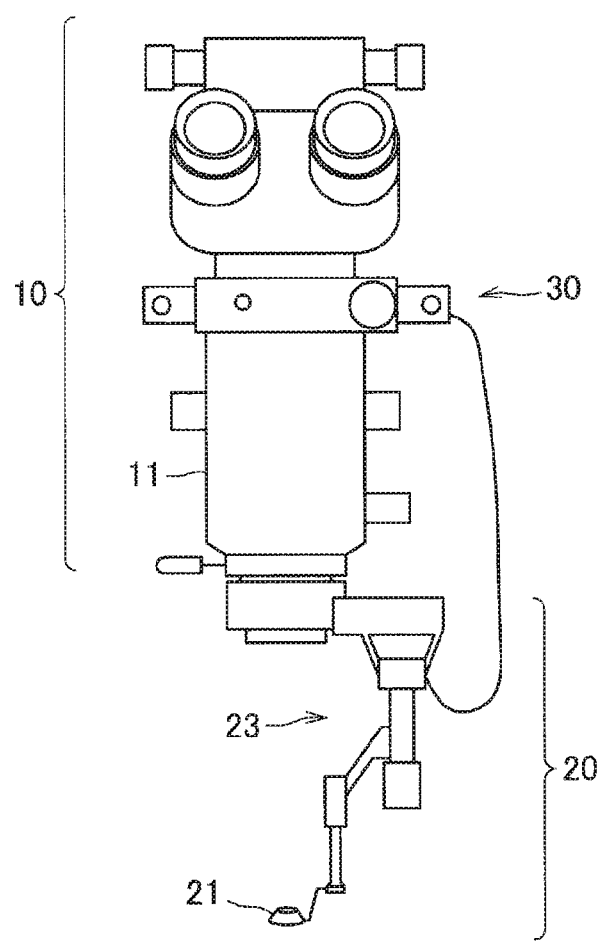
FIG. 3 is an explanatory view illustrating one example of the surgical microscope including a noncontact type wide-angle observation system used in the ophthalmic surgery microscope system according to the embodiment.

First, an ophthalmic surgery microscope system according to a first embodiment of the disclosure will be outlined with reference to FIGS. 1 to 3. FIG. 1 is an explanatory view illustrating a situation of ophthalmic surgery performed with an eye E of a subject being observed through a surgical microscope 10 by using an additional optical system 21 in an ophthalmic surgery microscope system 1 according to the first embodiment of the disclosure. FIG. 3 is an explanatory view illustrating changes in lateral magnification and vertical magnification of a real image caused by the additional optical system 21. FIG. 2 is an explanatory view illustrating one example of the surgical microscope 10 including a noncontact type wide-angle observation system 20 used in the ophthalmic surgery microscope system 1 according to the embodiment.

The ophthalmic surgery microscope system 1 according to the embodiment includes the surgical microscope 10, the additional optical system 21, an imaging unit, and a control unit. The surgical microscope 10 observes the inside of an eye from a pupil, and magnifies and presents a real image. The additional optical system 21 is selectively arranged between the surgical microscope 10 and the pupil. The imaging unit acquires the real image presented by the surgical microscope 10 as an image. The control unit changes a vertical magnification control value for adjusting the vertical magnification of the real image in accordance with a detection result of the additional optical system 21.

As illustrated in FIG. 1, retina and vitreous surgery, which is one type of ophthalmic surgery, is performed with the inside of the eye E of the subject being observed from a pupil 52 by using the surgical microscope 10 and the additional optical system 21. In the retina and vitreous surgery, first, an eyeball is opened under local anesthesia, and a trocar (not illustrated) is placed on a sclera 54. Then, a surgical instrument such as a lighting device 71, a vitreous body cutter 73, and a perfusate supplying device 75 is inserted into the eye through the trocar. For example, a vitreous body 55 is removed, a proliferating membrane is removed, or a detached retina 57 is reattached. At this time, the additional optical system 21 is switched in accordance with a purpose.

A concave lens 21a (on the left in FIG. 2) or a convex lens 21b (on the right in FIG. 2) is used as the additional optical system 21. The concave lens 21a cancels a refractive index (approximately 60D) of a cornea 51 and a crystalline lens 53. The convex lens 21b has a refractive index (e.g., 120D) stronger than those of the cornea 51 and the crystalline lens 53. In a case where the concave lens 21a is used, a fundus image A1 is directly observed through the surgical microscope 10. In contrast, in a case where the convex lens 21b, which is a wide-angle observation lens, is used, a real image (fundus image) B1 formed by the additional optical system 21 is observed through the surgical microscope 10. In the former case, only a narrow range (range A0) around the posterior pole of the fundus can be visually recognized. In contrast, in the latter case, a wide range (B0) of the fundus can be observed. For this reason, the additional optical system 21 is called a wide-angle observation system (or a wide-view system), and greatly contributes to the recent breakthrough in minimally invasive retina and vitreous surgery.

The wide-angle observation system includes a contact type and a noncontact type. In the contact type, the additional optical system 21 is placed and used on an eyeball. In the noncontact type, the wide-angle observation system is integrated with, for example, the surgical microscope 10 as illustrated in FIG. 3. The wide-angle observation system 20 of noncontact type includes, for example, the additional optical system 21 and a support mechanism 23. The support mechanism 23 is provided on a mirror body 11 of the surgical microscope 10, and supports the additional optical system 21. The support mechanism 23 supports the additional optical system 21 so that the additional optical system 21 is arranged on an optical axis of the surgical microscope 10. The support mechanism 23 can move the additional optical system 21 in an optical-axis direction for adjusting a focus. Control information of the wide-angle observation system 20 is output to a control device 30. As illustrated on the right in FIG. 2, an inverted image is observed in the wide-angle observation system 20. Consequently, the control device 30 may perform processing such as converting an inverted real image into an erect image in accordance with the installation of the additional optical system 21.

Here, it is known that a wide operative field can be obtained by the wide-angle observation system while feeling of unevenness is weakened. This is because the lateral magnification and the vertical magnification of a real image created by a convex lens, which is added as the additional optical system 21, are defined by the following expressions (1) and (2).

Lateral magnification=(refractive index of crystalline lens+refractive index of cornea)/refractive index of additional optical system  (1)

Vertical magnification=(horizontal magnification)$^2$  (2)

From the above expression (2), the vertical magnification is represented by the square of the lateral magnification, and thus the feeling of unevenness of the operative field is more lost when the wide field of view is obtained. Consequently, for example, in fine treatment (e.g., ILM peeling) for macula in the posterior pole part of fundus, many surgeons bother to perform switching to a concave lens in order to easily grasp feeling of distance between a surgical instrument and retina. It takes time to switch an additional optical system, however, the additional optical system cannot be instantaneously changed. Thus, the ophthalmic surgery microscope system 1 according to the embodiment compensates for the decrease in the vertical magnification of a real image on a wide-angle observation system. The ophthalmic surgery microscope system 1 according to the embodiment will be described below in more detail.

[1.2. Functional Configuration]

Figure 4:
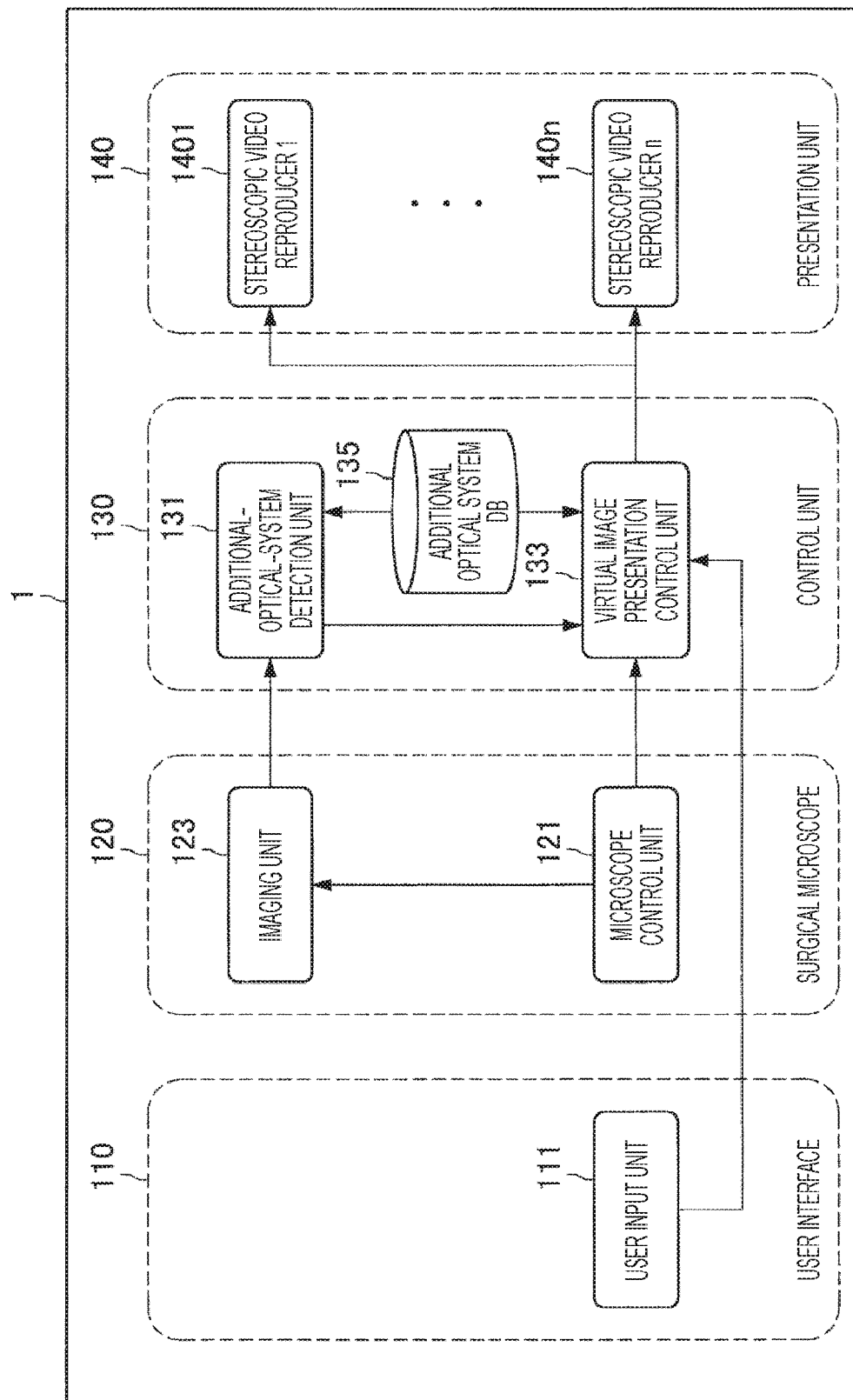
FIG. 4 is a block diagram illustrating the functional configuration of the ophthalmic surgery microscope system 1 according to the embodiment.
Figure 5:
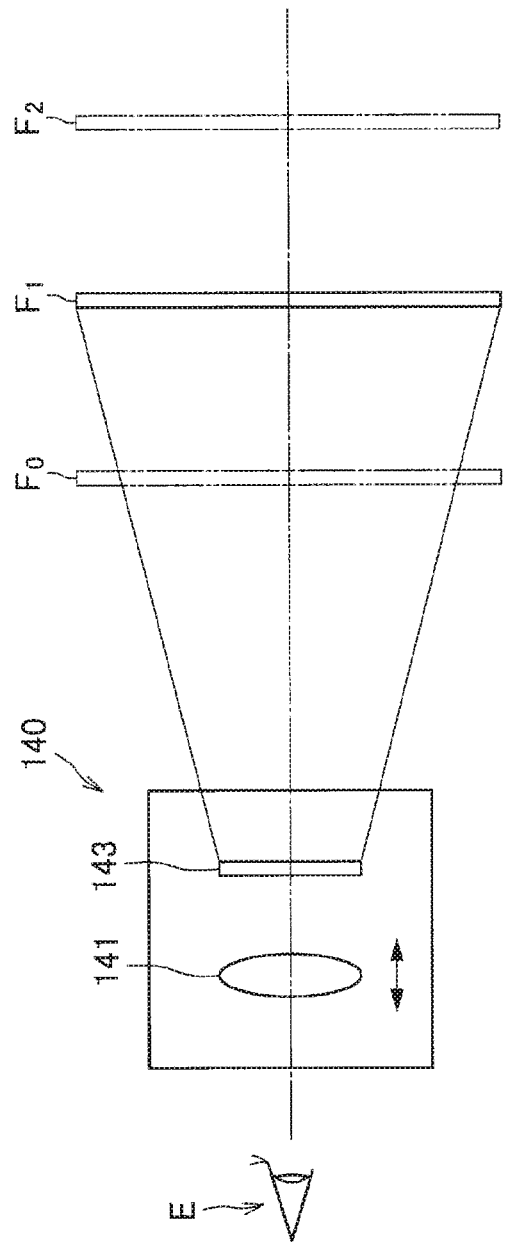
FIG. 5 is an explanatory view illustrating one example of a method of changing a virtual image position in a presentation unit.
Figure 6:
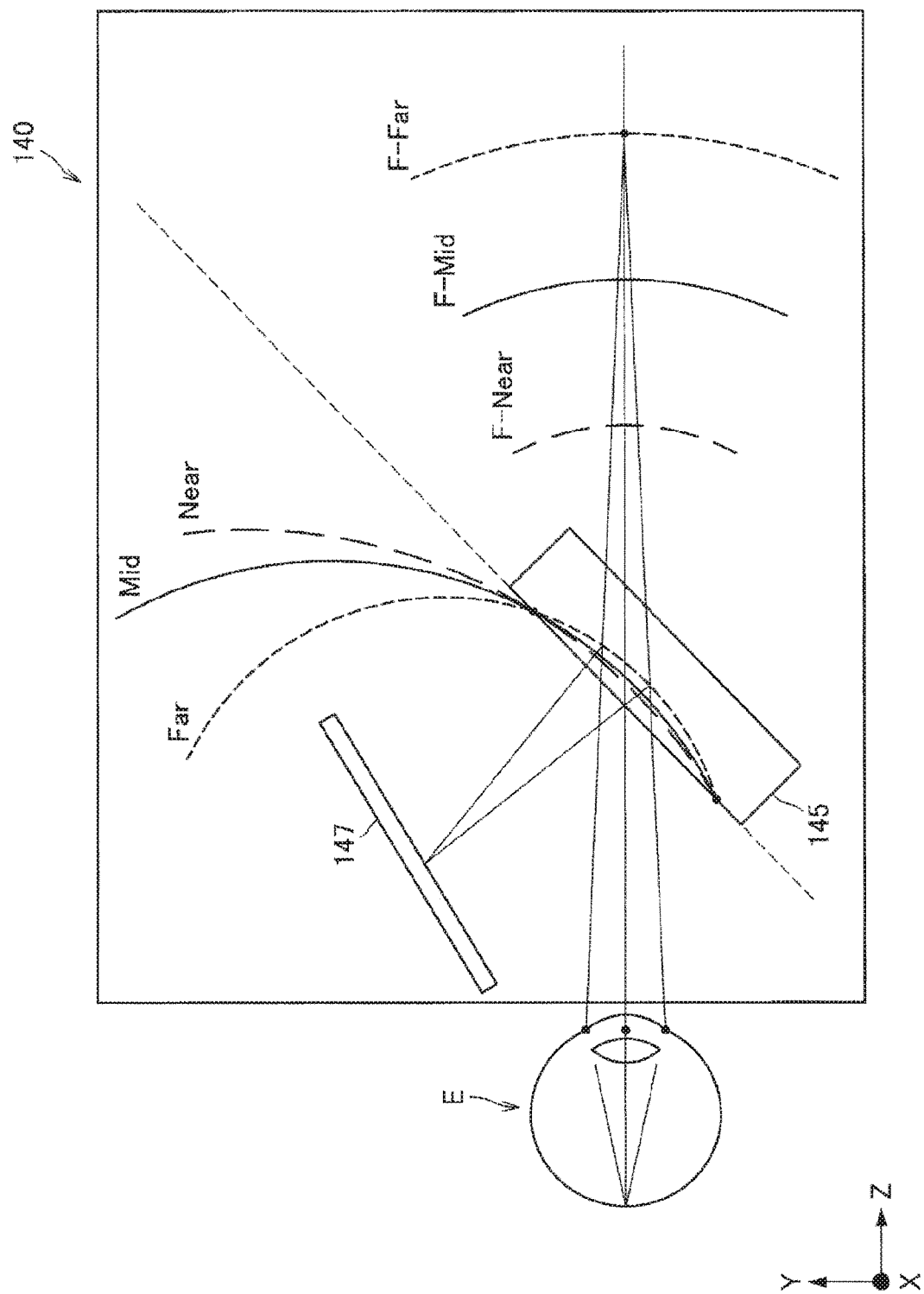
FIG. 6 is an explanatory view illustrating another example of the method of changing a virtual image position in the presentation unit.

The functional configuration of the ophthalmic surgery microscope system 1 according to the embodiment will be described with reference to FIGS. 4 to 6. FIG. 4 is a block diagram illustrating the functional configuration of the ophthalmic surgery microscope system 1 according to the embodiment. FIG. 5 is an explanatory view illustrating one example of a method of changing a virtual image position in a presentation unit 140. FIG. 6 is an explanatory view illustrating another example of the method of changing a virtual image position in the presentation unit 140.

As illustrated in FIG. 4, the ophthalmic surgery microscope system 1 according to the embodiment includes a user interface 110, a surgical microscope 120, a control unit 130, and the presentation unit 140.

(User Interface)

The user interface 110 includes a user input unit 111 that receives input of information from a user. The user can input a set value of a target vertical magnification by using, for example, the user input unit 111. The information input from the user input unit 111 is output to the control unit 130.

(Surgical Microscope)

The surgical microscope 120 is a device that magnifies and presents a real image, and corresponds to the surgical microscope 10 in FIGS. 1 to 3. The surgical microscope 120 according to the embodiment includes a microscope control unit 121 and an imaging unit 123. For example, in a case where an image acquired by the surgical microscope 120 is an inverted image, the microscope control unit 121 converts the inverted image to an erect image, and performs focus control for an image. The control information of the microscope control unit 121 is output to the control unit 130. The imaging unit 123 is mounted in the surgical microscope 120, and acquires an image as a stereo image. The image acquired by the imaging unit 123 is finally displayed on the presentation unit 140. The imaging unit 123 outputs the acquired image to the control unit 130.

(Control Unit)

The control unit 130 controls the virtual image position of an image presented on the presentation unit 140 in accordance with the additional optical system 21. The control unit 130 corresponds to the control device 30 in FIG. 1. The control unit 130 includes an additional-optical-system detection unit 131, a virtual image presentation control unit 133, and an additional optical system database (DB) 135.

The additional-optical-system detection unit 131 detects whether or not the additional optical system 21 is installed in the surgical microscope 120. For example, in a noncontact type wide-angle observation system integrally configured with the surgical microscope 120, the presence or absence of the installation of the additional optical system 21 can be acquired from the control information from the microscope control unit 121. Generally, in the noncontact type wide-angle observation system, an image conversion mechanism that converts an inverted image into an erect image functions in accordance and conjunction with the installation of the additional optical system 21. The presence or absence of the installation of the additional optical system 21 can be detected by detecting that the additional optical system 21 has been installed and the image conversion mechanism functions on the basis of the control information of such an image conversion mechanism.

In contrast, in a case where a contact type wide-angle observation system that is not integrated with the surgical microscope 120 is used, the additional-optical-system detection unit 131 cannot directly detect the presence or absence of the installation of the additional optical system 21 even if the additional optical system 21 is placed on cornea. In this case, the additional-optical-system detection unit 131 can detect the presence or absence of the installation of the additional optical system 21, for example, as follows.

For example, the additional-optical-system detection unit 131 can detect that the additional optical system 21 is installed by detecting that the microscope control unit 121 has performed the processing of converting an inverted image into an erect image. That is, since the installation of the additional optical system 21 requires conversion of the inverted image into the erect image, the user causes the image conversion mechanism to function via the user input unit 111. Then, the installation of the additional optical system 21 can be detected in response to the fact that the image conversion mechanism has functioned.

Alternatively, the installation of the additional optical system 21 can be detected by using focus information. In a case where the additional optical system 21 is installed, as illustrated on the right in FIG. 2, a real image created above the additional optical system 21 is observed through the surgical microscope 120. Consequently, the microscope control unit 121 greatly changes the focus of the surgical microscope 120 to the side opposite to a subject. Using this, the additional-optical-system detection unit 131 can detect the installation of the additional optical system 21 by detecting that the focus of the surgical microscope 120 has been greatly changed to the side opposite to the subject by a predetermined value or more. Alternatively, the installation of the additional optical system 21 can be detected by the distance between the surgical microscope 120 and the subject such as an eyeball being calculated on the basis of, for example, a stereo image acquired by the imaging unit 123 and the focus of the surgical microscope 120 being set to the side opposite to the subject than a position separated by the distance.

Moreover, the additional-optical-system detection unit 131 can also detect the installation of the additional optical system 21 by object recognition from the stereo image acquired by the imaging unit 123. Note that the additional-optical-system detection unit 131 can detect the installation of the additional optical system 21 by performing the object recognition by using not a stereo image but only one camera image (e.g., camera image acquired from one of two cameras).

In this way, the additional-optical-system detection unit 131 can detect the presence or absence of the installation of the additional optical system 21 by using the control information of the surgical microscope 120 or the image acquired by the imaging unit 123.

Moreover, the additional-optical-system detection unit 131 detects the presence or absence of the installation of the additional optical system 21, and, in a case where the additional optical system 21 is installed, acquires refractive index information of the additional optical system 21. For example, in a case of a noncontact type wide-angle observation system, the installed additional optical system 21 is fixed, and thus the refractive index information is also only required to be acquired together with the presence or absence of the installation. In a case where the refractive index information cannot be automatically acquired, for example, the user preliminarily inputs lens information of the additional optical system 21 to be used, and thereby the refractive index information may be acquired from the lens information with reference to the additional optical system DB 135.

Alternatively, the lens information can be acquired by reading information preliminarily marked on the additional optical system 21 by using an image acquired by the imaging unit 123, which is mounted in the surgical microscope 120. The information marked on the additional optical system 21 is associated with the lens information, and may be, for example, two-dimensional barcode information and the like. The information marked on the additional optical system 21 may be marked on, for example, the outer peripheral part or a central part of the additional optical system 21. In a case where the information is marked on the central part of the additional optical system 21, the information may be made to be observed, for example, only in a case where illumination light having a specific wavelength such as infrared light is applied, and may be detected by using an imaging device capable of detecting the corresponding specific wavelength.

The virtual image presentation control unit 133 controls the virtual image position at the time when the image acquired by the imaging unit 123 is presented on the presentation unit 140 in accordance with the additional optical system 21 detected by the additional-optical-system detection unit 131. Specifically, the virtual image presentation control unit 133 changes a vertical magnification control value in order to achieve a target vertical magnification set by the user in accordance with the additional optical system 21.

For example, in a case where the target vertical magnification is set to "2", the vertical magnification is only required to be set to "2" as it is in a case where the additional optical system 21 is not installed. In contrast, in a case where the additional optical system 21 is installed, the vertical magnification control value is set so that a decrease in the vertical magnification of a real image created by the additional optical system 21 is compensated for. For example, in a case where the additional optical system 21 has 120D, the lateral magnification is ½ while the vertical magnification is ¼, so that the aspect ratio is ½. In this case, setting the vertical magnification control value to "4" can compensate for the decrease in the vertical magnification.

Moreover, the real image created by the additional optical system 21 also depends on the refractive index of a cornea or a crystalline lens of the subject. Then, the virtual image presentation control unit 133 may acquire refractive index information of the subject or information regarding the presence or absence of the crystalline lens, and calculate the vertical magnification of the real image on the basis of the information. These pieces of information may be acquired with reference to, for example, the patient information database in which the refractive index information of the subject or patient information regarding the presence or absence of the crystalline lens is recorded. Alternatively, the presence or absence of the crystalline lens can be detected from, for example, an image acquired by the imaging unit 123. The vertical magnification control value may be calculated on the basis of the calculated vertical magnification of the real image by calculating the vertical magnification of the real image with reference to such information. As a result, the vertical magnification control value can be more finely adjusted.

Furthermore, the virtual image presentation control unit 133 may set the vertical magnification in accordance with a procedure. For example, the user can specify the vertical magnification for each procedure by using the user input unit 111. In a case where the ophthalmic surgery microscope system 1 is set to a vertical magnification specification mode in which the vertical magnification is set in accordance with a procedure, the virtual image presentation control unit 133 can recognize the procedure being performed from, for example, an image acquired by the imaging unit 123. As a result, the vertical magnification can be automatically increased in, for example, a procedure, in which feeling of the distance to a retina is important, such as ILM peeling at a macula part.

The virtual image presentation control unit 133 sets the vertical magnification control value in order to achieve a target vertical magnification, and then calculates the virtual image position of an image at the time of presentation to the presentation unit 140 on the basis of the vertical magnification control value. In the ophthalmic surgery microscope system 1 according to the embodiment, the virtual image position is only required to be calculated on the basis of control information from the surgical microscope 120, as in Patent Document 1, for example. In a case where the calculated convergence angle and the vertical magnification control value at the time of image display are respectively defined as θ and K, the virtual image presentation control unit 133 calculates a convergence angle θ' after correction by the following expression (3).

$$\theta' = \theta/K \tag{3}$$

Then, the virtual image presentation control unit 133 corrects the virtual image position so as to satisfy the convergence angle θ' after correction. As a result, the stereoscopic effect of the subject can be increased by K times as compared with that in a case where the additional optical system 21 is not installed, and the stereoscopic effect that has been lowered by the additional optical system 21 can be compensated for.

The virtual image presentation control unit 133 changes the optical system of the presentation unit 140 so that the virtual image of an image is displayed at the virtual image position calculated on the basis of the above expression (3), and displays the image on the presentation unit 140. For example, in a case where the presentation unit 140 is a head mounted display (hereinafter, referred to as an "HMD") as illustrated in FIG. 5, the HMD includes an eyepiece 141 and a display unit 143 arranged in the optical-axis direction for each of the left and right eyes E. At this time, an image can be changed to positions such as virtual image positions $F_0$, $F_1$, and $F_2$ by moving the eyepiece 141 in the optical-axis direction (e.g., JP Hei 8-194189 A). Alternatively, for example, as illustrated in FIG. 6, the virtual image position of the image displayed on a display 147 can be changed to, for example, F_Near, F_Mid, and F_Far by changing the curvature of a lens by using a membrane mirror 145.

Note that the method of changing a virtual image position by using the presentation unit 140 is not limited to the examples in FIGS. 5 and 6. The virtual image position may be changed by another method. Furthermore, the presentation unit 140 is not limited to the HMD. The presentation unit 140 may be any device capable of stereoscopically presenting an image, such as a 3D display. In a case where a 3D display is used as the presentation unit 140, the virtual image position of an image can be changed by physically moving the 3D display, for example. Consequently, in a case where a 3D display is used as the presentation unit 140, movement space is preferably secured sufficiently.

The additional optical system DB 135 stores information regarding the additional optical system 21, and the additional optical system DB 135 stores, for example, lens information of a lens that can be used as the additional optical system 21. For example, the bending rate information of the additional optical system is stored as the lens information.

(Presentation Unit)

The presentation unit 140 is a presentation device that stereoscopically presents an image acquired by the imaging unit 123 on the basis of a virtual image position adjusted by the control unit 130. The presentation unit 140 corresponds to a presentation device 40 in FIG. 1. As illustrated in FIG. 4, the ophthalmic surgery microscope system 1 includes one or a plurality of stereoscopic video reproducers 1401 to 140*n*. The stereoscopic video reproducers 1401 to 140*n* may be, for example, HMDs, 3D displays, or the like, as described above.

[1.3. Control Method]

Figure 7:
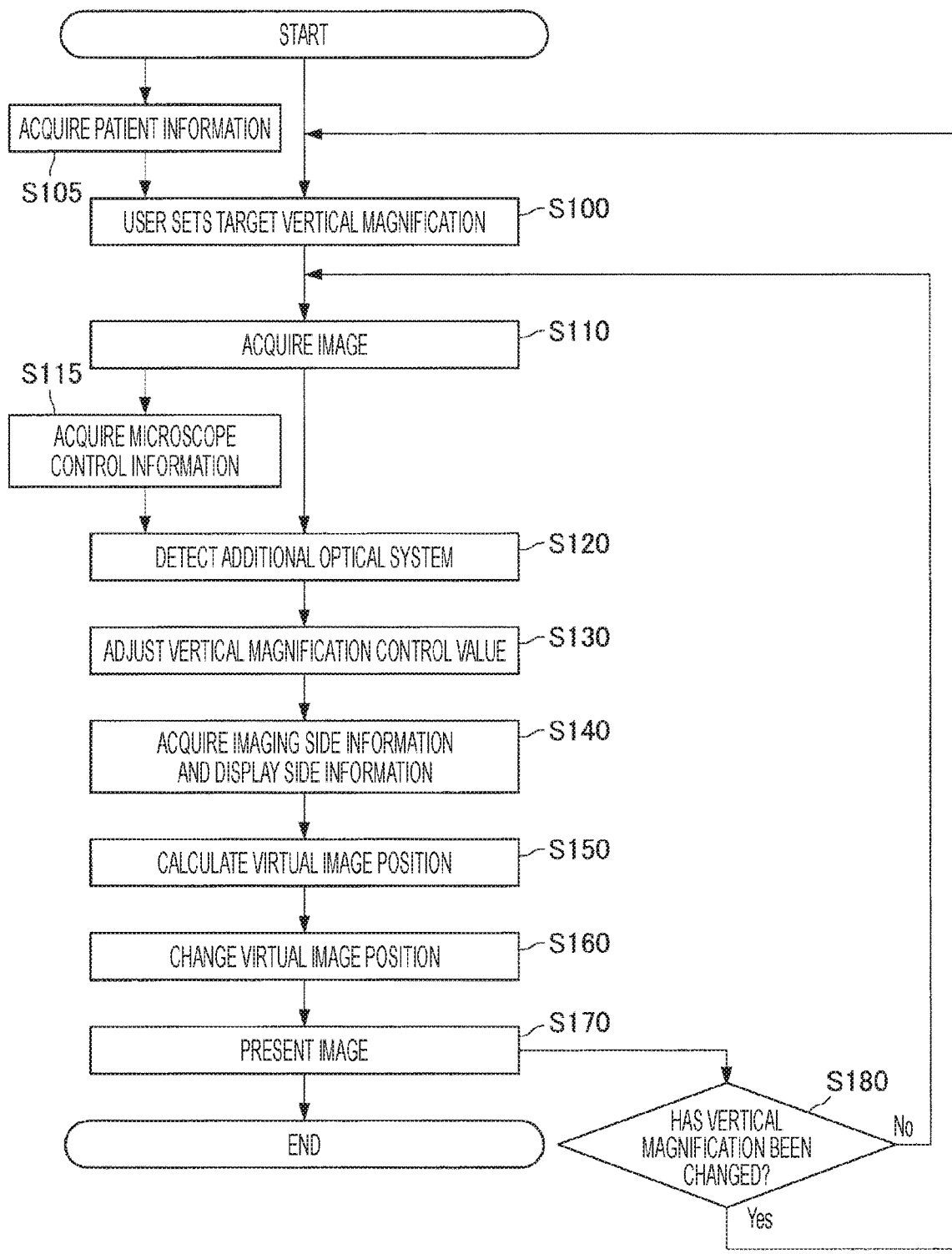
FIG. 7 is a flowchart illustrating processing for compensating for reduction in stereoscopic effects of an image in the ophthalmic surgery microscope system according to the embodiment.

Processing for compensating for reduction in stereoscopic effects of an image presented on the presentation unit 140 by the installation of the additional optical system 21 in the ophthalmic surgery microscope system 1 according to the embodiment will be described below with reference to FIG. 7. FIG. 7 is a flowchart illustrating processing for compensating for reduction in stereoscopic effects of an image in the ophthalmic surgery microscope system 1 according to the embodiment.

(Target Vertical Magnification Setting)

As illustrated in FIG. 7, a user first sets a target vertical magnification in the ophthalmic surgery microscope system 1 (S100). The user sets a desired vertical magnification by using the user input unit 111. At this time, for example, a lateral magnification at the time when an image presented on the presentation unit 140 appears to be the same as an actual object is defined as a reference value "1". In a case where the target vertical magnification is set to "2", an image appears to be doubly stretched in a depth direction. In a case where the target vertical magnification is set to "½", the image appears to be ½ times in the depth direction. The target vertical magnification may be preset to a desired value for each user, or may be set at any time through an interface such as a foot switch.

Alternatively, the target vertical magnification may be set in accordance with a procedure. In this case, the vertical magnification specification mode may be introduced in, for example, the ophthalmic surgery microscope system 1. In the vertical magnification specification mode, a procedure being performed is recognized, and a target vertical magnification is automatically specified on the basis of the recognized procedure. In this case, the setting of the target vertical magnification in Step S100 may be performed before the later-described processing (S130) of adjusting a vertical magnification control value after the imaging unit 123 acquires an image.

(Patient Information Acquisition)

Here, prior to Step S100, patient information may be acquired (S105). The patient information includes, for example, the refractive index of a cornea of a patient being a subject, the presence or absence of a crystalline lens, and a refractive index of an artificial crystalline lens in a case where the artificial crystalline lens is mounted. The patient information may be acquired by referring to a preliminarily measured and recorded patient information database, or may be measured and acquired before surgery. Step S105 is only required to be performed at least in a case where the patient information is used in the later-described processing (S130) of adjusting the vertical magnification control value. In a case where the processing of Step S105 is not performed, or in a case where the patient information cannot be acquired, a generally known value may be set as the patient information. For example, the refractive index of a cornea may be set to 40D, and the refractive index of a crystalline lens may be set to 20D, for example.

(Image Acquisition)

Then, the imaging unit 123 mounted on the surgical microscope 120 acquires an image of an operative field as a stereo image (S110). The image acquired by the imaging unit 123 is finally displayed on the presentation unit 140. The imaging unit 123 outputs the acquired image to the control unit 130.

(Detection of Additional Optical System)

Then, the additional-optical-system detection unit 131 detects whether or not the additional optical system 21 is installed in the surgical microscope 120 (S120). This is because the vertical magnification control value is changed on the basis of the presence or absence of the additional optical system 21 and, in a case where the additional optical system 21 is installed, the refractive index of the additional optical system 21.

As for the detection of the additional optical system 21, as illustrated above, for example, in a noncontact type wide-angle observation system integrally configured with the surgical microscope 120, the presence or absence of the installation of the additional optical system 21 can be acquired from the control information from the microscope control unit 121. Generally, in the noncontact type wide-angle observation system, an image conversion mechanism that converts an inverted image into an erect image functions in accordance and conjunction with the installation of the additional optical system 21. The presence or absence of installation of the additional optical system 21 can be detected by detecting that the additional optical system 21 has been installed and the image conversion mechanism functions on the basis of the control information of such an image conversion mechanism.

In contrast, in a case where a contact type wide-angle observation system that is not integrated with the surgical microscope 120 is used, the fact that processing of converting an inverted image into an erect image is performed at the microscope control unit 121 by an operation of the user can be detected, and the installation of the additional optical system 21 can be detected, for example. Alternatively, since the focus of the surgical microscope 120 is greatly changed to a side opposite to a subject in a case where the additional optical system 21 is installed, the installation of the additional optical system 21 can also be detected by using focus information. In these cases, the control information of the surgical microscope 120 is acquired (S115).

Moreover, the installation of the additional optical system 21 can be detected by object recognition from a stereo image acquired by the imaging unit 123. In this way, the additional-optical-system detection unit 131 can detect the presence or absence of the installation of the additional optical system 21 by using the control information of the surgical microscope 120 or the image acquired by the imaging unit 123. Note that the additional-optical-system detection unit 131 can detect the installation of the additional optical system 21 by performing the object recognition by using not a stereo image but only one camera image (e.g., camera image acquired from one of two cameras).

For example, in a case of a noncontact type wide-angle observation system, the refractive index information of the additional optical system 21 can be acquired together with the presence or absence of installation of the additional optical system 21. In a case where the refractive index information cannot be automatically acquired, for example, the user preliminarily inputs lens information of the additional optical system 21 to be used, and thereby the refractive index information may be acquired from the lens information with reference to the additional optical system DB 135. Alternatively, the lens information can be acquired by reading information preliminarily marked on the additional optical system 21 by using an image acquired by the imaging unit 123.

(Adjustment of Vertical Magnification Control Value)

Then, the virtual image presentation control unit 133 controls the virtual image position at the time when the image acquired by the imaging unit 123 is presented on the presentation unit 140 in accordance with the additional optical system 21 detected by the additional-optical-system detection unit 131. Consequently, first, the virtual image presentation control unit 133 changes a vertical magnification control value in order to achieve a target vertical magnification set by the user in accordance with the additional optical system 21 (S130).

For example, in a case where the target vertical magnification is set to "2", the vertical magnification is only required to be set to "2" as it is in a case where the additional optical system 21 is not installed. In contrast, in a case where the additional optical system 21 is installed, the vertical magnification control value is set so that a decrease in the vertical magnification of a real image created by the additional optical system 21 is compensated for. For example, in a case where the additional optical system 21 has 120D, the lateral magnification is ½ while the vertical magnification is ¼, so that the aspect ratio is ½. In this case, setting the vertical magnification control value to "4" can compensate for the decrease in the vertical magnification. Note that the vertical magnification of the real image created by the additional optical system 21 may be calculated by using the patient information of the subject acquired in Step S105. As a result, the vertical magnification control value can be more finely adjusted.

(Calculation of Virtual Image Position)

The virtual image presentation control unit 133 sets the vertical magnification control value in order to achieve a target vertical magnification. The virtual image presentation control unit 133 acquires information on an imaging side and a display side (S140). The virtual image presentation control unit 133 then calculates the virtual image position of an image at the time of presentation to the presentation unit 140 on the basis of the vertical magnification control value (S150). As described above, the virtual image position is only required to be calculated on the basis of the control information of the surgical microscope 120, as in Patent Document 1, for example. At this time, the virtual image presentation control unit 133 determines the convergence angle $\theta'$ after correction by using a calculated convergence angle $\theta$ and vertical magnification control value K at the time of image display in the above expression (3). Then, the virtual image presentation control unit 133 corrects the virtual image position so as to satisfy the convergence angle $\theta'$ after correction. As a result, the stereoscopic effect of the subject can be increased by K times as compared with that in a case where the additional optical system 21 is not installed, and the stereoscopic effect that has been lowered by the additional optical system 21 can be compensated for.

(Change of Virtual Image Position)

Then, the virtual image presentation control unit 133 changes the optical system of the presentation unit 140 so that a virtual image is displayed at the virtual image position calculated in Step S150, and displays the image on the presentation unit 140 (S160). In the ophthalmic surgery microscope system 1 according to the embodiment, the virtual image position is changed by changing the side of the presentation unit 140. Specifically, for example, as illustrated in FIG. 5, the virtual image is changed to positions such as the virtual image positions $F_0$, $F_1$, and $F_2$ by moving the eyepiece 141 of the HMD, which is one of the presentation units 140, in the optical-axis direction. Alternatively, for example, as illustrated in FIG. 6, the virtual image position of the image displayed on a display 147 may be changed to, for example, F_Near, F_Mid, and F_Far by changing the curvature of a lens by using a membrane mirror 145. Of course, the virtual image position may be changed by a method of changing a virtual image position other than those in FIGS. 5 and 6.

(Image Presentation)

Then, the virtual image presentation control unit 133 presents the image acquired by the imaging unit 123 by using the presentation unit 140 (S170). Note that, after that, whether or not the vertical magnification has been changed is determined (S180). In a case where the vertical magnification is not changed, processing from Step S110 is repeatedly executed. In contrast, in a case where the vertical magnification is changed, the processing returns to Step S100 to set the target vertical magnification, and the subsequent processing is repeatedly executed.

Processing for compensating for reduction in stereoscopic effects of an image presented on the presentation unit 140 by the installation of the additional optical system 21 in the ophthalmic surgery microscope system 1 according to the embodiment has been described above. According to the embodiment, a vertical magnification control value is calculated in accordance with the additional optical system 21, and a virtual image position of an image in the presentation unit 140 is calculated by using the vertical magnification control value. Then, the setting of the presentation unit 140 is changed so that a virtual image is displayed at the calculated virtual image position. This can compensate for the stereoscopic effect of an image, which is lost due to the installation of the additional optical system 21.

2. SECOND EMBODIMENT

Next, an ophthalmic surgery microscope system 1 according to a second embodiment of the disclosure will be described with reference to FIGS. 8 to 11. The ophthalmic surgery microscope system 1 according to the embodiment is different from the ophthalmic surgery microscope system 1 according to the first embodiment in that the vertical magnification of an image presented on the basis of the vertical magnification control value is adjusted on the imaging side. In the following description, differences from the ophthalmic surgery microscope system 1 according to the first embodiment will be mainly described, and detailed description of the same configuration and the same function will be omitted.

[2.1. Functional Configuration]

Figure 8:
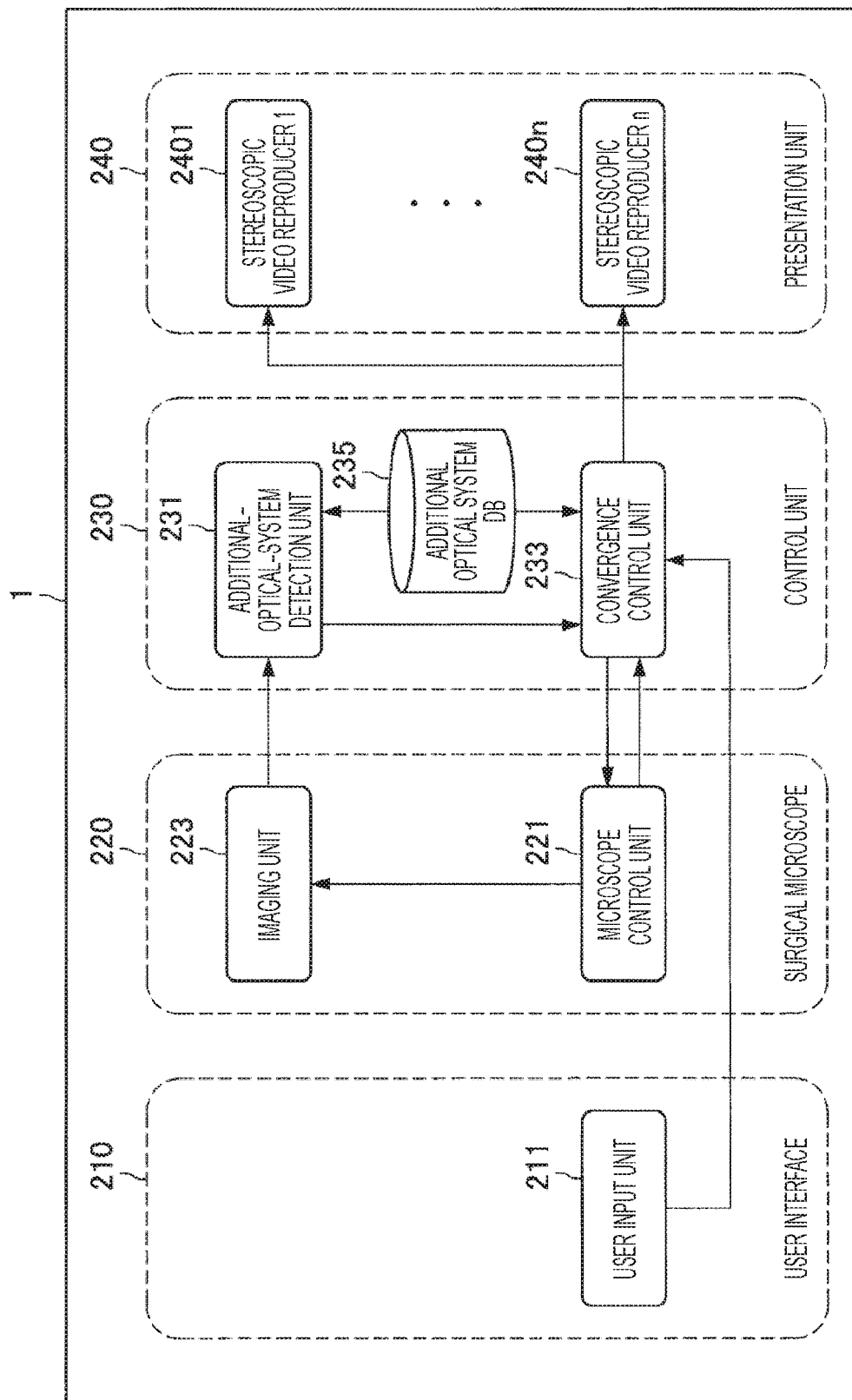
FIG. 8 is a block diagram illustrating the functional configuration of an ophthalmic surgery microscope system 1 according to a second embodiment of the disclosure.
Figure 9:
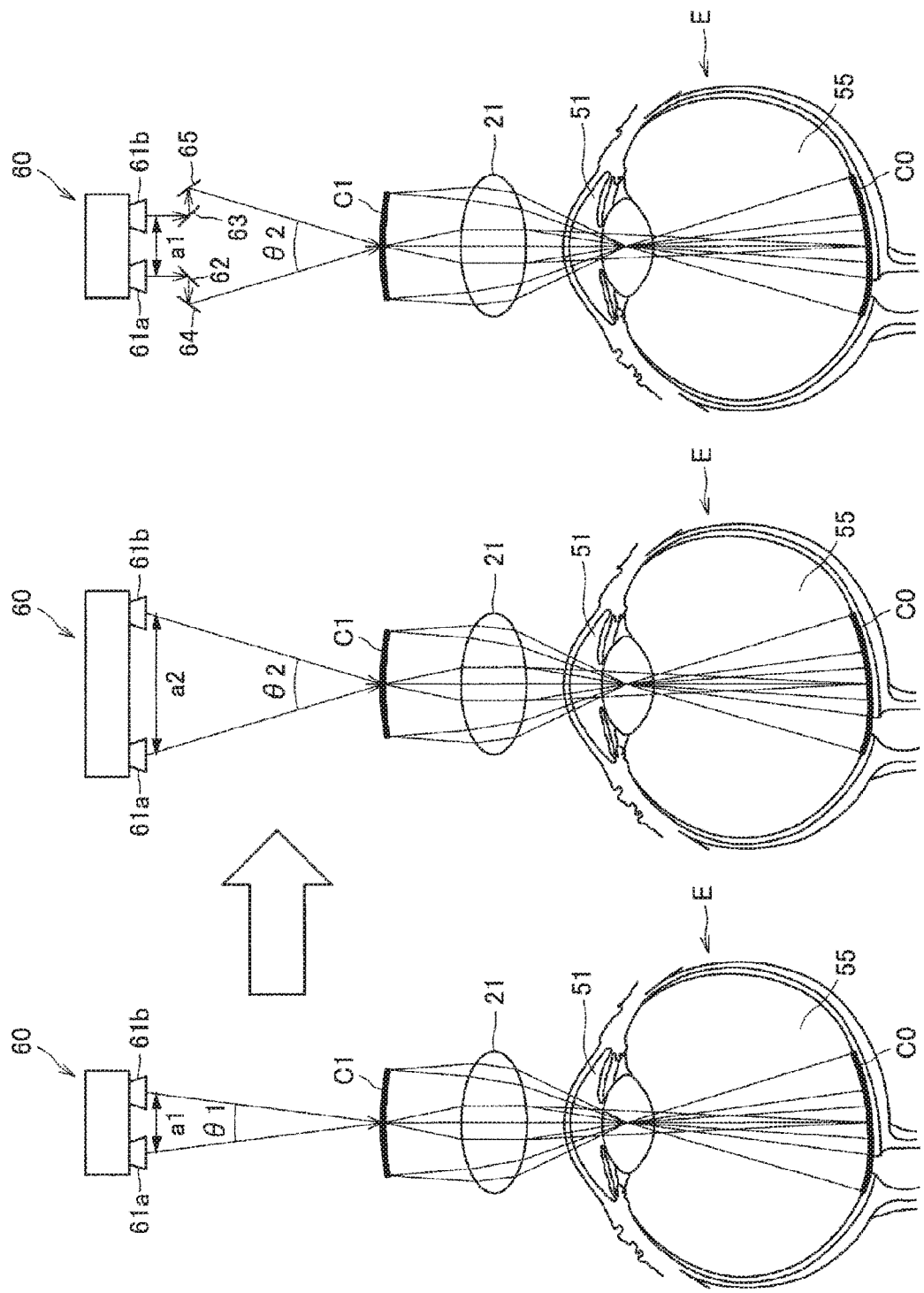
FIG. 9 is an explanatory view illustrating one example of a method of changing convergence in an imaging unit.
Figure 10:
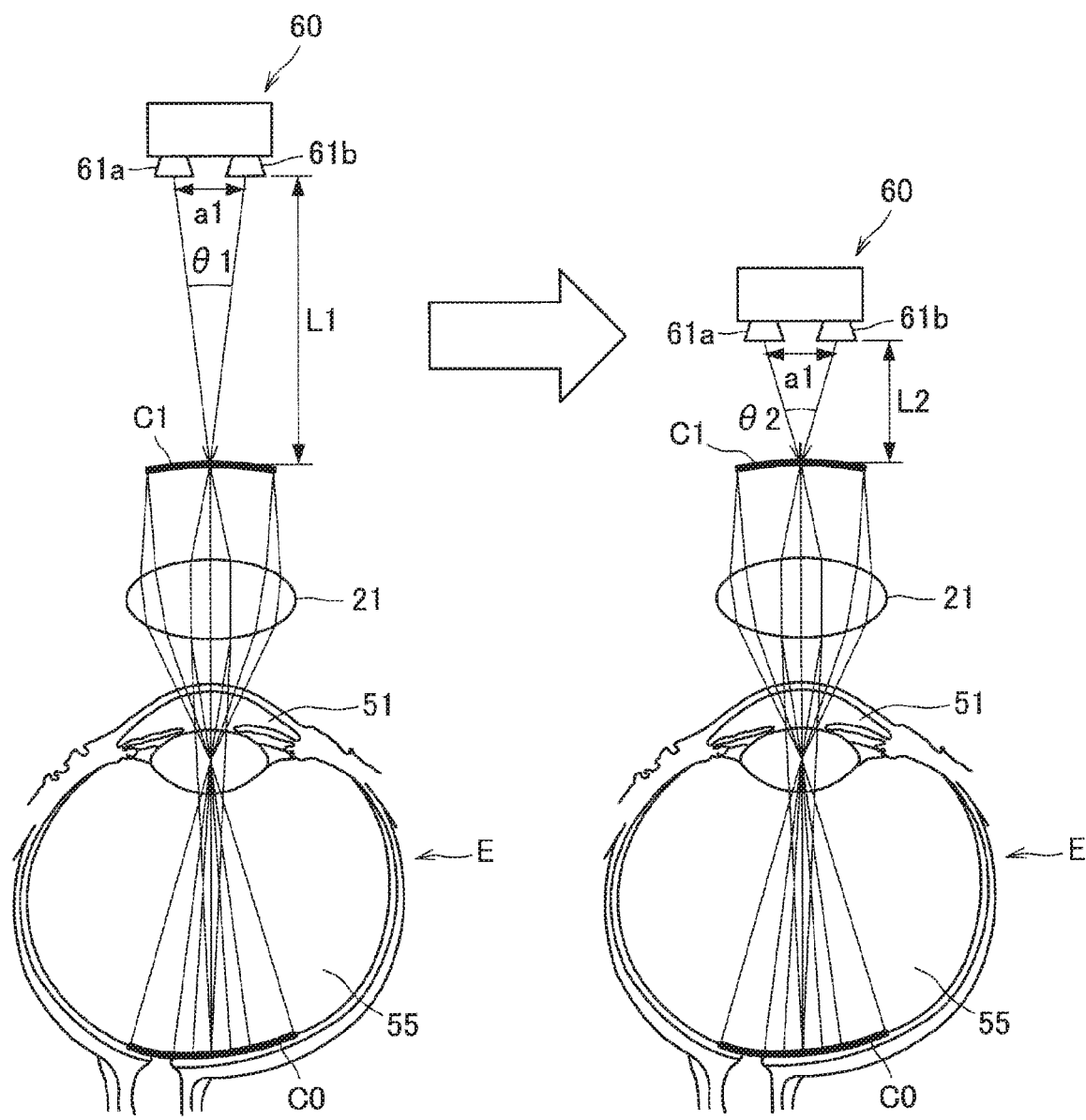
FIG. 10 is an explanatory view illustrating another example of a method of changing convergence in the imaging unit.

First, the functional configuration of the ophthalmic surgery microscope system 1 according to the embodiment will be described with reference to FIGS. 8 to 10. FIG. 8 is a block diagram illustrating the functional configuration of the ophthalmic surgery microscope system 1 according to the embodiment. FIG. 9 is an explanatory view illustrating a method of changing convergence by changing a baseline length in an imaging unit 223. FIG. 10 is an explanatory view illustrating a method of changing convergence by changing an imaging distance in the imaging unit 223.

As illustrated in FIG. 8, the ophthalmic surgery microscope system 1 according to the embodiment includes a user interface 210, a surgical microscope 220, a control unit 230, and a presentation unit 240. The user interface 210, the surgical microscope 220, the control unit 230, and the presentation unit 240 correspond to the user interface 110, the surgical microscope 120, the control unit 130, and the presentation unit 140 of the ophthalmic surgery microscope system 1 according to the first embodiment, respectively. In the ophthalmic surgery microscope system 1 according to the embodiment, the convergence of the imaging unit 223 is changed in accordance with the presence or absence of the installation of the additional optical system 21 and, in a case where the additional optical system 21 is installed, lens information of the additional optical system 21. This compensates for the vertical magnification of an image presented by the presentation unit 240 in a case where the additional optical system 21 is installed.

(User Interface)

The user interface 210 includes a user input unit 211 that receives input of information from a user. The user interface 210 has a configuration similar to that of the user interface 110 according to the first embodiment.

(Surgical Microscope)

The surgical microscope 220 is a device that magnifies and presents a real image, and corresponds to the surgical microscope 10 in FIGS. 1 to 3. The surgical microscope 220 according to the embodiment includes a microscope control unit 221 and the imaging unit 223. Although these functions are equivalent to those of the surgical microscope 120 according to the first embodiment, the imaging unit 223 is configured to be able to change convergence.

It is assumed that the imaging unit 223 is a stereo camera 60 including two cameras 61a and 61b as illustrated in FIGS. 9 and 10, for example. At this time, the convergence of the imaging unit 223 may be changed by changing the baseline length, which is the distance between the two cameras 61a and 61b as illustrated in FIG. 9, for example. As illustrated in FIG. 10, the convergence of the imaging unit 223 may be changed by changing the distance (imaging distance) between a real image C1 and the cameras 61a and 61b. In the former case, for example, in order to increase the convergence angle θ1 to θ2, a baseline length a1 is only required to be increased to a2. At this time, as illustrated in the center of FIG. 9, the convergence angle may be set to θ2 by widening the distance between the two cameras 61a and 61b. Alternatively, as illustrated on the right in FIG. 9, the convergence angle may be set to θ2 by providing mirrors 62, 63, 64, and 65 between the two cameras 61a and 61b and the real image C1. The mirrors 62, 63, 64, and 65 change an optical path. In the latter case, as illustrated in FIG. 10, the convergence angle may be set to θ2 while an imaging distance L1 between the real image C1 and the cameras 61a and 61b is changed to L2.

The convergence of the imaging unit 223 is changed in this way by the microscope control unit 221 controlling the imaging unit 223 on the basis of the control amount calculated by a convergence control unit 233 of the control unit 230.

(Control Unit)

The control unit 230 controls a virtual image position of an image to be presented at the presentation unit 240 in accordance with the additional optical system 21. The control unit 230 includes an additional-optical-system detection unit 231, the convergence control unit 233, and an additional optical system database (DB) 235. The additional-optical-system detection unit 231 and the additional optical system DB 235 are configured similarly to the additional-optical-system detection unit 131 and the additional optical system DB 135 according to the first embodiment.

The convergence control unit 233 calculates a convergence control value for changing the convergence of the imaging unit 223 in accordance with the additional optical system 21 detected by the additional-optical-system detection unit 231. The convergence is changed, and an image is acquired. The stereoscopic effect at the time of presenting the acquired image on the presentation unit 240 is compensated for. Specifically, the convergence control value is, for example, a control value of the baseline length in FIG. 9 or a control value of the imaging distance in FIG. 10.

First, the convergence control unit 233 changes a vertical magnification control value in order to achieve a target vertical magnification set by a user. Such processing is similar to that of the first embodiment. The target vertical magnification may be set in accordance with a procedure. The convergence control unit 233 sets the vertical magnification control value in order to achieve a target vertical magnification, and then calculates convergence of the imaging unit 223 after the change on the basis of the vertical magnification control value. The convergence of the imaging unit 223 after the change is only required to be calculated on the basis of the above expression (3). Then, the convergence control unit 233 changes the convergence of the imaging unit 223 so as to satisfy the convergence angle θ' after correction. As a result, the stereoscopic effect of a subject can be increased by K times as compared with that in a case where the additional optical system 21 is not installed, and an image, in which stereoscopic effect lowered by the additional optical system 21 is compensated for, can be acquired by the imaging unit 223.

(Presentation Unit)

The presentation unit 240 is a presentation device that stereoscopically presents an image acquired by the imaging unit 223. As in the first embodiment, as illustrated in FIG. 8, the ophthalmic surgery microscope system 1 includes one or a plurality of stereoscopic video reproducers 2401 to 240*n*. The stereoscopic video reproducers 2401 to 240*n* may be, for example, HMDs, 3D displays, or the like, as described above.

[2.2. Control Method]

Figure 11:
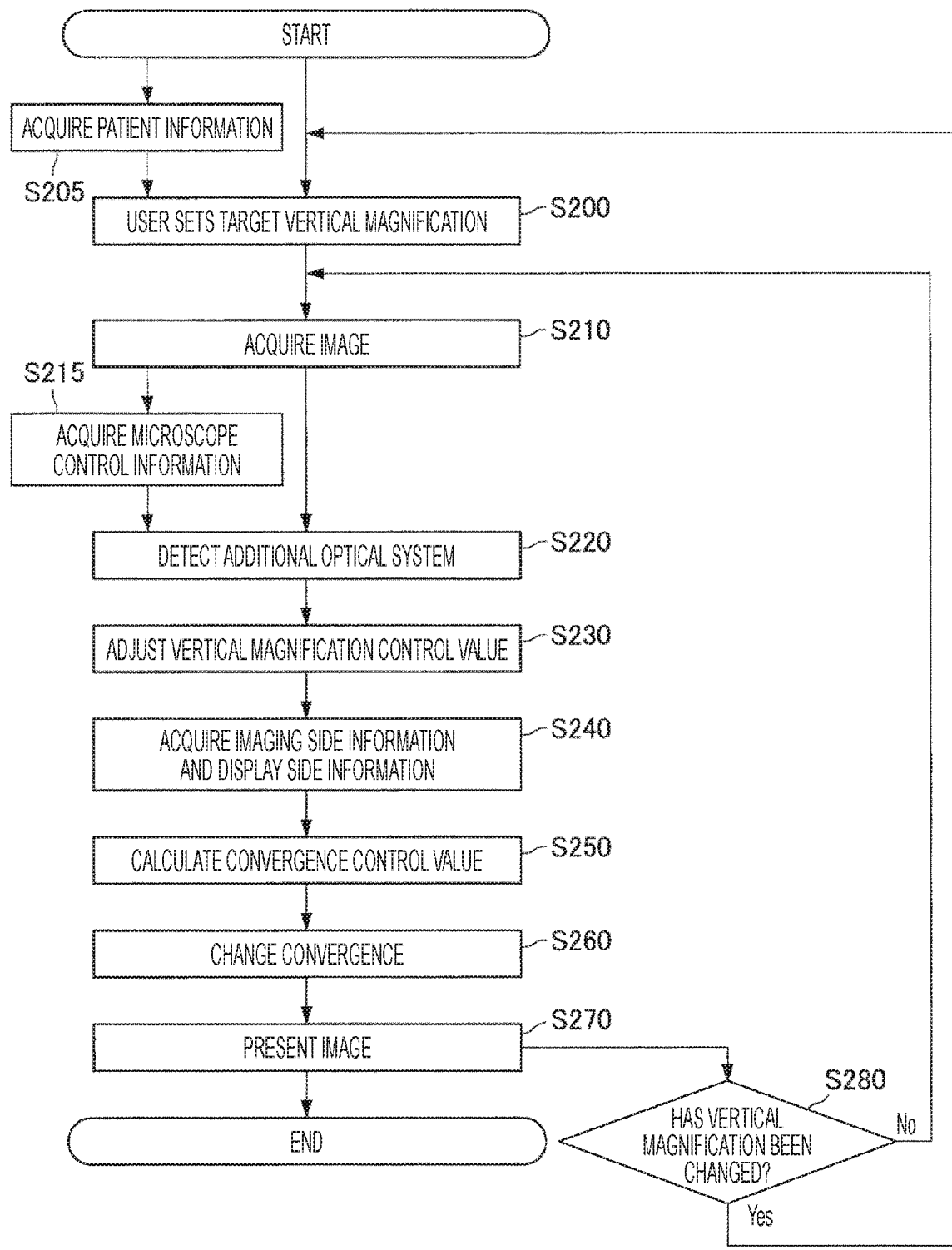
FIG. 11 is a flowchart illustrating processing for compensating for reduction in stereoscopic effects of an image in the ophthalmic surgery microscope system according to the embodiment.

Processing for compensating for reduction in stereoscopic effects of an image presented on the presentation unit 240 by the installation of the additional optical system 21 in the ophthalmic surgery microscope system 1 according to the embodiment will be described below with reference to FIG. 11. FIG. 11 is a flowchart illustrating processing for compensating for reduction in stereoscopic effects of an image in the ophthalmic surgery microscope system 1 according to the embodiment.

(Target Vertical Magnification Setting)

As illustrated in FIG. 11, a user first sets a target vertical magnification in the ophthalmic surgery microscope system 1 (S200). The user sets a desired vertical magnification by using the user input unit 211. Such processing is only required to be performed similarly to the target vertical magnification setting processing (S100) according to the first embodiment in FIG. 7.

(Patient Information Acquisition)

Here, prior to Step S200, patient information may be acquired (S205). The patient information includes, for example, the refractive index of a cornea of a patient being a subject, the presence or absence of a crystalline lens, and a refractive index of an artificial crystalline lens in a case where the artificial crystalline lens is mounted. Such processing is only required to be performed similarly to the patient information acquisition processing (S105) according to the first embodiment in FIG. 7.

(Image Acquisition)

Then, the imaging unit 223 mounted on the surgical microscope 220 acquires an image of an operative field as a stereo image (S210). The image acquired by the imaging unit 223 is finally displayed on the presentation unit 240. At this time, the imaging unit 223 acquires an image after the convergence is changed on the basis of the detection result of the additional optical system 21 by the later-described processing of Steps S220 to S260. The imaging unit 223 outputs the acquired image to the control unit 230.

(Detection of Additional Optical System)

Furthermore, the additional-optical-system detection unit 231 detects whether or not the additional optical system 21 is installed in the surgical microscope 220 (S220). This is because the vertical magnification control value is changed on the basis of the presence or absence of the additional optical system 21 and, in a case where the additional optical system 21 is installed, the refractive index of the additional optical system 21. Such processing is only required to be performed similarly to processing (S120) of detecting the additional optical system according to the first embodiment in FIG. 7.

(Adjustment of Vertical Magnification Control Value)

Then, the convergence control unit 233 changes the convergence of the imaging unit 223 at the time when the imaging unit 223 acquires an image in accordance with the additional optical system 21 detected by the additional-optical-system detection unit 231. Consequently, first, the convergence control unit 233 changes a vertical magnification control value in order to achieve a target vertical magnification set by the user in accordance with the additional optical system 21 (S230). Such processing is only required to be performed similarly to the processing (S130) of adjusting the vertical magnification control value according to the first embodiment in FIG. 7.

(Calculation of Convergence Control Value)

The convergence control unit 233 sets the vertical magnification control value in order to achieve a target vertical magnification. The convergence control unit 233 acquires information on an imaging side and a display side (S240). The convergence control unit 233 then calculates the convergence control value of the imaging unit 223 on the basis of the vertical magnification control value (S250). The convergence after correction can be obtained by determining the convergence angle θ' after the correction by using a calculated convergence angle θ and vertical magnification control value K at the time of image display in the above expression (3). Then, the convergence control unit 233 calculates the convergence control value of the imaging unit 223 so as to satisfy the convergence angle θ' after the correction. As illustrated in FIG. 9, in a case where the convergence is changed by changing the baseline length of the imaging unit 223, the convergence control unit 233 calculates the control value of the baseline length. In a case where the convergence is changed by changing the imaging distance in FIG. 10, the convergence control unit 233 calculates the control value of the imaging distance. As a result, the stereoscopic effect of the subject can be increased by K times as compared with that in a case where the additional optical system 21 is not installed, and an image in which the stereoscopic effect lowered by the additional optical system 21 is compensated for can be acquired.

(Change of Convergence and Image Presentation)

Then, the convergence control unit 233 changes the baseline length or the imaging distance of the imaging unit 223 on the basis of the convergence control value calculated in Step S250 (S260). In the image in which the convergence of the imaging unit 223 has been adjusted, the stereoscopic effect that has been lowered by the additional optical system 21 is compensated for. The presentation unit 240 presents the image acquired by the imaging unit 223 (S270). Then, whether or not the vertical magnification has been changed is determined (S280). In a case where the vertical magnification is not changed, processing from Step S210 is repeatedly executed. In contrast, in a case where the vertical magnification is changed, the processing returns to Step S200 to set the target vertical magnification, and the subsequent processing is repeatedly executed.

Processing for compensating for reduction in stereoscopic effects of an image presented on the presentation unit 240 by the installation of the additional optical system 21 in the ophthalmic surgery microscope system 1 according to the embodiment has been described above. According to the embodiment, a vertical magnification control value is calculated in accordance with the additional optical system 21, and the convergence of the imaging unit 223 at the time of acquiring an image is calculated by using the vertical magnification control value. Then, the imaging unit 223 is adjusted so as to satisfy the calculated convergence. As a result, in the image acquired by the imaging unit 223, the stereoscopic effect of the image lost by the installation of the additional optical system 21 is compensated for.

3. CONCLUSION

The configuration and the function of the ophthalmic surgery microscope system 1 according to the disclosure have been described above. According to the ophthalmic surgery microscope system 1 described above, the vertical magnification of an image lost at the time when a wide-angle observation system is used can be compensate for in accordance with the detection of the additional optical system 21, and a wide operative field image of fundus can be presented without impairing stereoscopic effects. Even in a case where the noncontact type additional optical system 21 is used, the additional optical system 21 can be detected, and the vertical magnification can be appropriately compensated for.

Furthermore, the vertical magnification can be more appropriately compensated for by calculating the vertical magnification control value in further consideration of the presence or absence of the crystalline lens of a subject or lens information of the additional optical system 21. Moreover, in the ophthalmic surgery microscope system 1 according to the disclosure, the target vertical magnification can be set in accordance with a procedure, and the vertical magnification control value can be calculated on the basis of the target vertical magnification. This makes it possible to provide an operative field image in which the vertical magnification is appropriately enlarged even in a procedure in which feeling of the distance to retina is particularly important, such as processing for a macula part.

The target vertical magnification can be set to an appropriate value in accordance with the preference of each user. Furthermore, for example, in a case where an HMD is used as a presentation unit, the vertical magnification can be adjusted for each individual who uses the HMD. Consequently, individual approach can be taken. In the individual approach, for example, the vertical magnification of an image to be presented for an assistant or a supervisory doctor is set lower than that of an image to be presented for a surgeon who actually operates a surgical instrument, thereby reducing fatigue.

Note that, in the first embodiment, the vertical magnification of an image to be presented is compensated for by adjusting a virtual image position by adjusting the reproduction side that presents an image, that is, the presentation unit. In the second embodiment, the vertical magnification of an image to be presented is compensated for by adjusting the convergence of the imaging side of an image, that is, the imaging unit. In the ophthalmic surgery microscope system 1 according to the disclosure, these approaches for compensating for the vertical magnification of an image to be presented may be combined. For example, in a case where the former approach is performed alone, there are restrictions in an adjustable range of, for example, an ocular and a membrane mirror, and it is thus possible that these components cannot be moved to specified positions. Furthermore, in a case where the latter approach is performed alone, the baseline length or the imaging distance of the imaging unit may need to be extremely changed, and a system may grow in size. Thus, combining these approaches can enhance the degree of freedom of adjustment for compensating for the stereoscopic effect of an image compared to the case where each approach is performed alone.

4. HARDWARE CONFIGURATION

Figure 12:
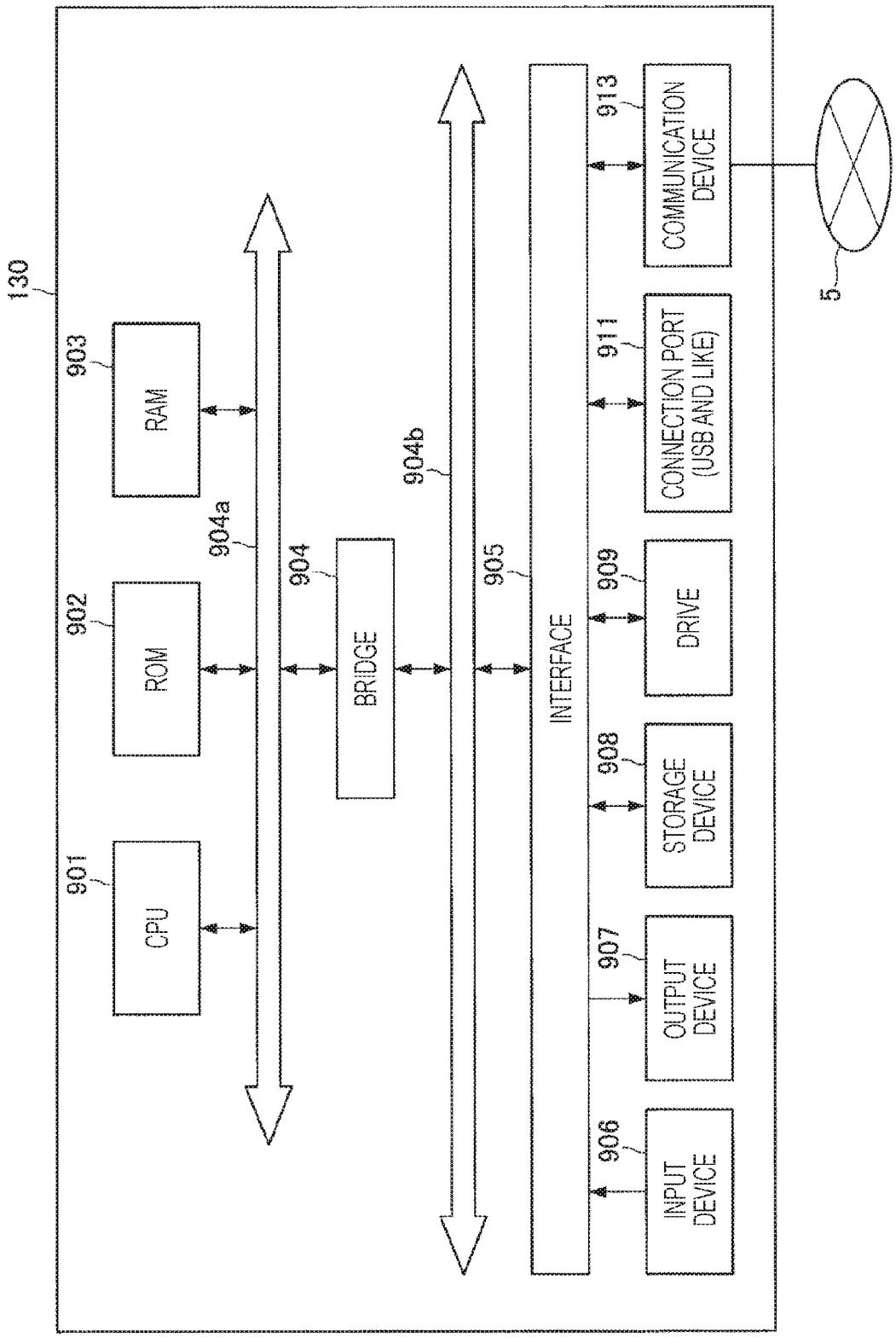
FIG. 12 is a hardware configuration diagram illustrating the hardware configuration of a control unit according to the embodiment.

The hardware configuration example of the control units 130 and 230 of the ophthalmic surgery microscope system 1 according to the above-described embodiment will be described. Since these devices can have similar configurations, the control unit 130 will be described below as an example. FIG. 12 is a hardware configuration diagram illustrating the hardware configuration of the control unit 130 according to the above-described embodiment.

As described above, the control unit 130 according to the embodiment can be implemented by a processing device such as a computer. As illustrated in FIG. 12, the control unit 130 includes a central processing unit (CPU) 901, a read only memory (ROM) 902, a random access memory (RAM) 903, and a host bus 904*a*. Furthermore, the control unit 130 includes a bridge 904, an external bus 904*b*, an interface 905, an input device 906, an output device 907, a storage device 908, a drive 909, a connection port 911, and a communication device 913.

The CPU 901 functions as an arithmetic processing device and a control device, and controls overall operation in the control unit 130 in accordance with various programs. Furthermore, the CPU 901 may be a microprocessor. For example, programs and arithmetic parameters used by the CPU 901 are stored in the ROM 902. The RAM 903 temporarily stores, for example, programs used in execution of the CPU 901 or parameters that appropriately change in the execution. These components are connected to each other by the host bus 904*a* including, for example, a CPU bus.

The host bus 904*a* is connected to the external bus 904*b* such as a peripheral component interconnect/interface (PCI) bus via the bridge 904. Note that the host bus 904*a*, the bridge 904, and the external bus 904*b* do not necessarily need to be separately configured, and these functions may be mounted on one bus.

The input device 906 includes, for example, an input apparatus and an input control circuit. A user uses the input apparatus for inputting information. The input apparatus includes, for example, a mouse, a keyboard, a touch panel, a button, a microphone, a switch, and a lever. The input control circuit generates an input signal on the basis of the input from the user, and outputs the input signal to the CPU 901. The output device 907 includes a display device and a voice output device. The display device includes, for example, a liquid crystal display (LCD) device, an organic light emitting diode (OLED) device, and a lamp. The voice output device includes, for example, a speaker.

The storage device 908 is one example of a storage unit of the control unit 130, and stores data. The storage device 908 may include a storage medium, a recording device, a reading device, a deleting device, and the like. The recording device records data in the storage medium. The reading device reads the data from the storage medium. The deleting device deletes the data recorded in the storage medium. The storage device 908 drives a hard disk, and stores a program to be executed by the CPU 901 and various pieces of data.

The drive 909 is a reader/writer for a storage medium, and is incorporated in or externally mounted on the control unit 130. The drive 909 reads information recorded in an attached removable storage medium, and outputs the information to the RAM 903. The removable recording medium includes, for example, a magnetic disk, an optical disk, a magneto-optical disk, and a semiconductor memory.

The connection port 911 is an interface connected to an external device, and is a connection port for an external device capable of transmitting data by, for example, a universal serial bus (USB) and the like. Furthermore, the communication device 913 is a communication interface including, for example, a communication device for connection to a communication network 5. Furthermore, the communication device 913 may be a wireless local area network (LAN) compatible communication device, a wireless USB compatible communication device, or a wire communication device that performs communication by wire.

Although the preferred embodiments of the disclosure have been described in detail above with reference to the accompanying drawings, the technical scope of the disclosure is not limited to such examples. It is obvious that a person having ordinary skill in the art of the disclosure can arrive at various alternations or modifications within the scope of the technical ideas set forth in the claims. These alternations or modifications are understood to naturally fall within the technical scope of the disclosure.

Furthermore, the effects described herein are merely illustrative or exemplary, and not limitative. That is, the technique according to the disclosure may have other effects that are obvious to a skilled person from the description of the specification, together with or in place of the above-described effects.

Note that, the configurations as described below also fall within the technical scope of the disclosure.

(1)
An ophthalmic surgery microscope system including:
a surgical microscope that observes an inside of an eye from a pupil, and magnifies and presents a real image;
an additional optical system selectively arranged between the surgical microscope and the pupil;
an imaging unit that acquires the real image presented by the surgical microscope as an image;
a presentation unit that stereoscopically presents the image; and
a control unit that changes a vertical magnification control value for adjusting a vertical magnification of the real image in accordance with a detection result of the additional optical system.

(2)
The ophthalmic surgery microscope system according to (1),
in which the control unit detects presence or absence of the additional optical system on the basis of control information of the surgical microscope or the image.

(3)
The ophthalmic surgery microscope system according to (1) or (2),
in which the control unit acquires refractive index information of the additional optical system.

(4)
The ophthalmic surgery microscope system according to any one of (1) to (3),
in which the control unit changes the vertical magnification control value on the basis of a target vertical magnification set by a user.

(5)
The ophthalmic surgery microscope system according to any one of (1) to (3),
in which the control unit changes the vertical magnification control value in accordance with a procedure.

(6)
The ophthalmic surgery microscope system according to any one of (1) to (5),
in which the control unit changes the vertical magnification control value on the basis of a vertical magnification of the real image calculated on the basis of refractive index information of a cornea of a subject or presence-or-absence information of a crystalline lens.

(7)
The ophthalmic surgery microscope system according to any one of (1) to (6),
in which the control unit controls a virtual image position of the image in the presentation unit on the basis of the set vertical magnification control value.

(8)
The ophthalmic surgery microscope system according to any one of (1) to (7),
in which the control unit adjusts convergence of the imaging unit on the basis of the set vertical magnification control value.

(9)
The ophthalmic surgery microscope system according to (8),
in which convergence of the imaging unit is adjusted by changing a baseline length or an imaging distance to the real image.

(10)
A control device including a control unit that:
detects an additional optical system selectively arranged between a surgical microscope and a pupil, the surgical microscope observing an inside of an eye from the pupil, and magnifying and presenting a real image;
changes a vertical magnification control value for adjusting a vertical magnification of the real image in accordance with a detection result of the additional optical system; and
adjusts a vertical magnification of an image of the real image acquired by the imaging unit on the basis of the vertical magnification control value.

(11)
A control method including:
detecting an additional optical system selectively arranged between a surgical microscope and a pupil, the surgical microscope observing an inside of an eye from the pupil, and magnifying and presenting a real image;
changing a vertical magnification control value for adjusting a vertical magnification of the real image in accordance with a detection result of the additional optical system; and
adjusting a vertical magnification of an image of the real image acquired by the imaging unit on the basis of the vertical magnification control value.

REFERENCE SIGNS LIST

1 Ophthalmic surgery microscope system
10 Surgical microscope
11 Mirror body
20 Wide-angle observation system
21 Additional optical system
21a Concave lens
21b Convex lens
23 Support mechanism
30 Control device
40 Presentation device
51 Cornea
52 Pupil
53 Crystalline lens
54 Sclera
55 Vitreous body
57 Retina
60 Stereo camera
61a, 61b Camera
62 to 65 Mirror
71 Lighting device
73 Vitreous body cutter
75 Perfusate supplying device 110, 210 User interface
111, 211 User input unit
120, 220 Surgical microscope
121, 221 Microscope control unit
123, 223 Imaging unit
130, 230 Control unit
131, 231 Additional-optical-system detection unit
133 Virtual image presentation control unit
135, 235 Additional optical system database (DB)
140, 240 Presentation Unit
141 Eyepiece
143 Display unit
145 Membrane mirror
147 Display
233 Convergence control unit

The invention claimed is:

1. An ophthalmic surgery microscope system, comprising:
 a surgical microscope that observes an inside of an eye from a pupil, and magnifies and presents a real image;
 an additional optical system selectively arranged between the surgical microscope and the pupil;
 an imaging unit that acquires the real image presented by the surgical microscope as an image;
 a presentation unit that stereoscopically presents the image; and
 a control unit that changes a vertical magnification control value to adjust a vertical magnification of the real image in accordance with a detection result of the additional optical system.

2. The ophthalmic surgery microscope system according to claim 1,
 wherein the control unit detects presence or absence of the additional optical system on a basis of control information of the surgical microscope or the image.

3. The ophthalmic surgery microscope system according to claim 1,
 wherein the control unit acquires refractive index information of the additional optical system.

4. The ophthalmic surgery microscope system according to claim 1,
 wherein the control unit changes the vertical magnification control value on a basis of a target vertical magnification set by a user.

5. The ophthalmic surgery microscope system according to claim 1,
 wherein the control unit changes the vertical magnification control value in accordance with a procedure.

6. The ophthalmic surgery microscope system according to claim 1,
 wherein the control unit changes the vertical magnification control value on a basis of a vertical magnification of the real image calculated on a basis of refractive index information of a cornea of a subject or presence-or-absence information of a crystalline lens.

7. The ophthalmic surgery microscope system according to claim 1, wherein the control unit controls a virtual image position of the image in the presentation unit on a basis of the changed vertical magnification control value.

8. The ophthalmic surgery microscope system according to claim 1, wherein the control unit adjusts convergence of the imaging unit on a basis of the changed vertical magnification control value.

9. The ophthalmic surgery microscope system according to claim 8,
 wherein convergence of the imaging unit is adjusted by changing a baseline length or an imaging distance to the real image.

10. A control device, comprising a control unit that:
 detects an additional optical system selectively arranged between a surgical microscope and a pupil, the surgical microscope observing an inside of an eye from the pupil, and magnifying and presenting a real image;
 changes a vertical magnification control value to adjust a vertical magnification of the real image in accordance with a detection result of the additional optical system; and
 adjusts a vertical magnification of an image of the real image acquired by the imaging unit on a basis of the vertical magnification control value.

11. A control method, comprising:
 detecting an additional optical system selectively arranged between a surgical microscope and a pupil, the surgical microscope observing an inside of an eye from the pupil, and magnifying and presenting a real image;
 changing a vertical magnification control value for adjusting a vertical magnification of the real image in accordance with a detection result of the additional optical system; and
 adjusting a vertical magnification of an image of the real image acquired by the imaging unit on a basis of the vertical magnification control value.

* * * * *